(12) United States Patent
Lorenzo et al.

(10) Patent No.: US 11,648,375 B2
(45) Date of Patent: May 16, 2023

(54) SYSTEM AND METHOD FOR DELIVERING A CATHETER

(71) Applicant: DePuy Synthes Products, Inc., Raynham, MA (US)

(72) Inventors: Juan Lorenzo, Davie, FL (US); Kirk Johnson, Raynham, MA (US); Dillon Karg, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 245 days.

(21) Appl. No.: 17/085,503

(22) Filed: Oct. 30, 2020

(65) Prior Publication Data
US 2021/0046283 A1 Feb. 18, 2021

Related U.S. Application Data

(62) Division of application No. 15/407,728, filed on Jan. 17, 2017, now Pat. No. 10,905,853.

(51) Int. Cl.
*A61M 25/01* (2006.01)
*A61M 25/09* (2006.01)
(Continued)

(52) U.S. Cl.
CPC ........ *A61M 25/01* (2013.01); *A61M 25/0023* (2013.01); *A61M 25/0054* (2013.01);
(Continued)

(58) Field of Classification Search
CPC .. A61M 2025/0687; A61M 2025/0175; A61M 29/00; A61M 25/0662; A61M 2029/025; A61M 5/16827; A61M 5/2066
See application file for complete search history.

(56) References Cited

U.S. PATENT DOCUMENTS

| | | |
|---|---|---|
| 5,320,602 A | 6/1994 | Karpiel |
| 5,389,087 A | 2/1995 | Miraki et al. |

(Continued)

FOREIGN PATENT DOCUMENTS

| | | |
|---|---|---|
| CN | 102159277 A | 8/2011 |
| JP | 2011-505201 A | 2/2011 |

(Continued)

OTHER PUBLICATIONS

Notification of Reasons for Refusal issued in Japanese Patent Application No. 2019-537436 dated Aug. 3, 2021, English translation only.

(Continued)

*Primary Examiner* — Tasnim Mehjabin Ahmed
(74) *Attorney, Agent, or Firm* — Troutman Pepper Hamilton Sanders LLP

(57) ABSTRACT

A method of delivering a catheter to a location of interest in the vasculature, the method including positioning a self-expanding sheath within a lumen of the catheter; advancing the catheter and the self-expanding sheath in tandem over a guidewire; and distally moving a distal end of the self-expanding sheath out from the lumen of the catheter thereby causing the self-expanding sheath to move from a collapsed state within the catheter to an expanded state outside the catheter, wherein when the self-expanding sheath is in the expanded state both the self-expanding sheath and the catheter are distally advanceable in tandem.

19 Claims, 9 Drawing Sheets

(51) Int. Cl.
*A61M 25/04* (2006.01)
*A61M 25/00* (2006.01)
*A61M 25/06* (2006.01)
*A61M 29/00* (2006.01)

(52) U.S. Cl.
CPC ........ *A61M 25/04* (2013.01); *A61M 25/0662* (2013.01); *A61M 25/09* (2013.01); *A61M 29/00* (2013.01); *A61M 2025/0024* (2013.01); *A61M 2025/0175* (2013.01); *A61M 2025/0681* (2013.01); *A61M 2025/09166* (2013.01); *A61M 2205/32* (2013.01)

(56) References Cited

U.S. PATENT DOCUMENTS

| | | | |
|---|---|---|---|
| 5,447,503 | A | 9/1995 | Miller |
| 5,569,296 | A | 10/1996 | Marin et al. |
| 5,697,948 | A | 12/1997 | Marin et al. |
| 5,709,658 | A | 1/1998 | Sirhan et al. |
| 5,857,464 | A | 1/1999 | Desai |
| 5,902,333 | A | 5/1999 | Roberts et al. |
| 5,947,925 | A | 9/1999 | Ashiya et al. |
| 6,059,748 | A | 5/2000 | Teirstein et al. |
| 6,120,480 | A | 9/2000 | Zhang et al. |
| 6,391,037 | B1 | 5/2002 | Greenhalgh |
| 6,527,789 | B1 | 3/2003 | Lau et al. |
| 6,692,482 | B2 | 2/2004 | Heller et al. |
| 7,144,386 | B2 | 12/2006 | Korkor et al. |
| 7,731,707 | B2 | 6/2010 | Heller et al. |
| 8,597,454 | B2 | 12/2013 | Parker et al. |
| 9,232,992 | B2 | 1/2016 | Heidner |
| 9,532,792 | B2 | 1/2017 | Galdonik et al. |
| 9,532,873 | B2 | 1/2017 | Kelley |
| 9,533,344 | B2 | 1/2017 | Monetti et al. |
| 9,539,011 | B2 | 1/2017 | Chen et al. |
| 9,539,022 | B2 | 1/2017 | Bowman |
| 9,539,122 | B2 | 1/2017 | Burke et al. |
| 9,539,382 | B2 | 1/2017 | Nelson |
| 9,549,830 | B2 | 1/2017 | Bruszewski et al. |
| 9,554,805 | B2 | 1/2017 | Tompkins et al. |
| 9,561,125 | B2 | 2/2017 | Bowman et al. |
| 9,572,982 | B2 | 2/2017 | Burnes et al. |
| 9,579,484 | B2 | 2/2017 | Barnell |
| 9,585,642 | B2 | 3/2017 | Dinsmoor et al. |
| 9,615,832 | B2 | 4/2017 | Bose et al. |
| 9,615,951 | B2 | 4/2017 | Bennett et al. |
| 9,622,753 | B2 | 4/2017 | Cox |
| 9,636,115 | B2 | 5/2017 | Henry et al. |
| 9,636,439 | B2 | 5/2017 | Chu et al. |
| 9,642,675 | B2 | 5/2017 | Werneth et al. |
| 9,655,633 | B2 | 5/2017 | Leynov et al. |
| 9,655,645 | B2 | 5/2017 | Staunton |
| 9,655,989 | B2 | 5/2017 | Cruise et al. |
| 9,662,129 | B2 | 5/2017 | Galdonik et al. |
| 9,662,238 | B2 | 5/2017 | Dwork et al. |
| 9,662,425 | B2 | 5/2017 | Lilja et al. |
| 9,668,898 | B2 | 6/2017 | Wong |
| 9,675,477 | B2 | 6/2017 | Thompson |
| 9,675,782 | B2 | 6/2017 | Connolly |
| 9,676,022 | B2 | 6/2017 | Ensign et al. |
| 9,692,557 | B2 | 6/2017 | Murphy |
| 9,693,852 | B2 | 7/2017 | Lam et al. |
| 9,700,262 | B2 | 7/2017 | Janik et al. |
| 9,700,399 | B2 | 7/2017 | Acosta-Acevedo |
| 9,717,421 | B2 | 8/2017 | Griswold et al. |
| 9,717,500 | B2 | 8/2017 | Tieu et al. |
| 9,717,502 | B2 | 8/2017 | Teoh et al. |
| 9,724,103 | B2 | 8/2017 | Cruise et al. |
| 9,724,526 | B2 | 8/2017 | Strother et al. |
| 9,750,565 | B2 | 9/2017 | Bloom et al. |
| 9,757,260 | B2 | 9/2017 | Greenan |
| 9,764,111 | B2 | 9/2017 | Gulachenski |
| 9,770,251 | B2 | 9/2017 | Bowman et al. |
| 9,770,577 | B2 | 9/2017 | Li et al. |
| 9,775,621 | B2 | 10/2017 | Tompkins et al. |
| 9,775,706 | B2 | 10/2017 | Paterson et al. |
| 9,775,732 | B2 | 10/2017 | Khenansho |
| 9,788,800 | B2 | 10/2017 | Mayoras, Jr. |
| 9,795,391 | B2 | 10/2017 | Saatchi et al. |
| 9,801,980 | B2 | 10/2017 | Karino et al. |
| 9,808,599 | B2 | 11/2017 | Bowman et al. |
| 9,833,252 | B2 | 12/2017 | Sepetka et al. |
| 9,833,604 | B2 | 12/2017 | Lam et al. |
| 9,833,625 | B2 | 12/2017 | Waldhauser et al. |
| 2002/0072712 | A1 | 6/2002 | Nool et al. |
| 2003/0078473 | A1 | 4/2003 | Richardson |
| 2005/0085746 | A1 | 4/2005 | Adams et al. |
| 2006/0064151 | A1 | 3/2006 | Guterman |
| 2007/0021685 | A1 | 1/2007 | Oepen et al. |
| 2008/0281350 | A1 | 11/2008 | Sepetka |
| 2009/0018525 | A1 | 1/2009 | Waite et al. |
| 2009/0143851 | A1 | 6/2009 | Paul, Jr. |
| 2010/0324649 | A1 | 12/2010 | Mattsson |
| 2011/0319917 | A1 | 12/2011 | Ferrera et al. |
| 2012/0065585 | A1 | 3/2012 | O'Dea |
| 2012/0283768 | A1 | 11/2012 | Cox et al. |
| 2013/0253474 | A1 | 9/2013 | Farhangnia |
| 2014/0135812 | A1 | 5/2014 | Divino et al. |
| 2014/0200607 | A1 | 7/2014 | Sepetka et al. |
| 2015/0081007 | A1* | 3/2015 | Joye ........................ A61F 2/856 623/1.11 |
| 2015/0257774 | A1 | 9/2015 | Galdonik et al. |
| 2015/0297250 | A1* | 10/2015 | Farhat ..................... A61F 2/966 606/200 |
| 2016/0235464 | A1 | 8/2016 | Fischell et al. |
| 2017/0007264 | A1 | 1/2017 | Cruise et al. |
| 2017/0007265 | A1 | 1/2017 | Guo et al. |
| 2017/0020540 | A1* | 1/2017 | Chou ..................... A61M 25/04 |
| 2017/0020670 | A1 | 1/2017 | Murray et al. |
| 2017/0020700 | A1 | 1/2017 | Bienvenu et al. |
| 2017/0027640 | A1 | 2/2017 | Kunis et al. |
| 2017/0027692 | A1 | 2/2017 | Bonhoeffer et al. |
| 2017/0027725 | A1 | 2/2017 | Argentine |
| 2017/0035436 | A1 | 2/2017 | Morita |
| 2017/0035567 | A1 | 2/2017 | Duffy |
| 2017/0042548 | A1 | 2/2017 | Lam |
| 2017/0049596 | A1 | 2/2017 | Schabert |
| 2017/0071737 | A1 | 3/2017 | Kelley |
| 2017/0072452 | A1 | 3/2017 | Monetti et al. |
| 2017/0079671 | A1 | 3/2017 | Morero et al. |
| 2017/0079680 | A1 | 3/2017 | Bowman |
| 2017/0079766 | A1 | 3/2017 | Wang et al. |
| 2017/0079767 | A1 | 3/2017 | Leon-Yip |
| 2017/0079812 | A1 | 3/2017 | Lam et al. |
| 2017/0079817 | A1 | 3/2017 | Sepetka et al. |
| 2017/0079819 | A1 | 3/2017 | Pung et al. |
| 2017/0079820 | A1 | 3/2017 | Lam et al. |
| 2017/0086851 | A1 | 3/2017 | Wallace et al. |
| 2017/0086996 | A1 | 3/2017 | Peterson et al. |
| 2017/0095259 | A1 | 4/2017 | Tompkins et al. |
| 2017/0100126 | A1 | 4/2017 | Bowman et al. |
| 2017/0100141 | A1 | 4/2017 | Morero et al. |
| 2017/0100143 | A1 | 4/2017 | Granfield |
| 2017/0100183 | A1 | 4/2017 | Iaizzo et al. |
| 2017/0113023 | A1 | 4/2017 | Steingisser et al. |
| 2017/0147765 | A1 | 5/2017 | Mehta |
| 2017/0151032 | A1 | 6/2017 | Loisel |
| 2017/0165062 | A1 | 6/2017 | Rothstein |
| 2017/0165065 | A1 | 6/2017 | Rothstein et al. |
| 2017/0165454 | A1 | 6/2017 | Tuohy et al. |
| 2017/0172581 | A1 | 6/2017 | Bose et al. |
| 2017/0172766 | A1 | 6/2017 | Vong et al. |
| 2017/0172772 | A1 | 6/2017 | Khenansho |
| 2017/0189033 | A1 | 7/2017 | Sepetka et al. |
| 2017/0189035 | A1 | 7/2017 | Porter |
| 2017/0215902 | A1 | 8/2017 | Leynov et al. |
| 2017/0216484 | A1 | 8/2017 | Cruise et al. |
| 2017/0224350 | A1 | 8/2017 | Shimizu et al. |
| 2017/0224355 | A1 | 8/2017 | Bowman et al. |
| 2017/0224467 | A1 | 8/2017 | Piccagli et al. |
| 2017/0224511 | A1 | 8/2017 | Dwork et al. |
| 2017/0224953 | A1 | 8/2017 | Tran et al. |
| 2017/0231749 | A1 | 8/2017 | Perkins et al. |

(56) References Cited

U.S. PATENT DOCUMENTS

| | | |
|---|---|---|
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

FOREIGN PATENT DOCUMENTS

| | | |
|---|---|---|
| JP | 2012-510352 A | 5/2012 |
| WO | 2011089014 A1 | 7/2011 |

OTHER PUBLICATIONS

International Search Report dated Mar. 29, 2018 during the prosecution of International Application No. PCT/IB2018/050291.
Communication pursuant to Article 94(3) EPC issued in European Patent Application No. 18 702 333.8 dated Dec. 6, 2021.
Search Report issued in corresponding Chinese Patent Application No. 201880007335.2 dated Feb. 18, 2021, English translation only.

* cited by examiner

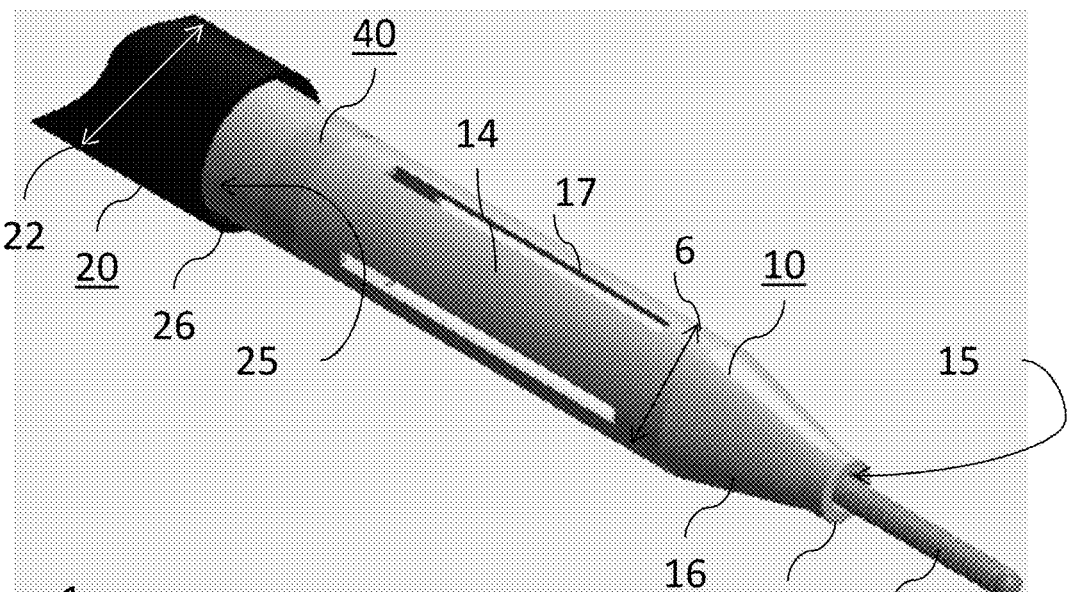
FIG. 1
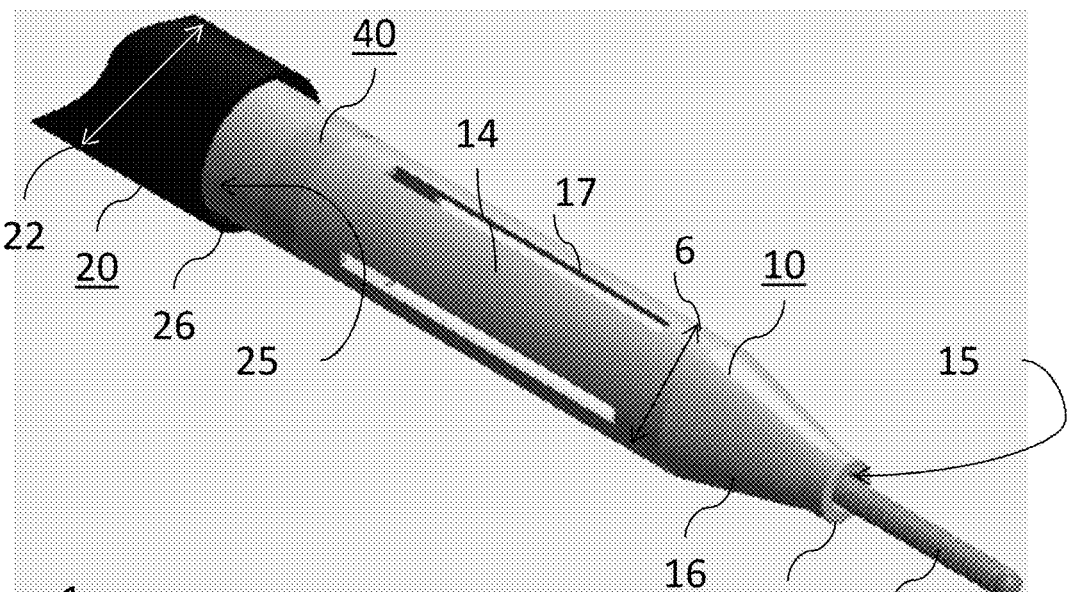
FIG. 2
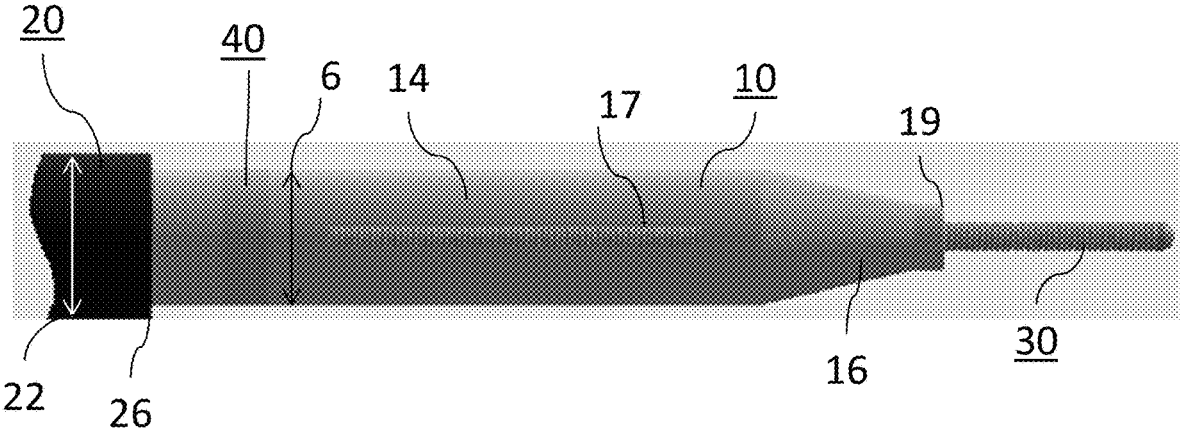
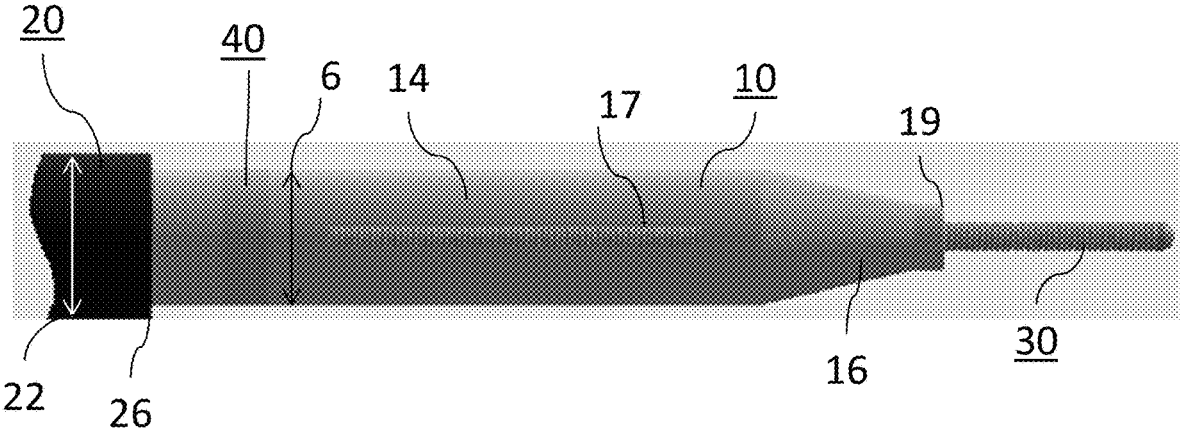

- 201 Selectively positioning a guidewire at a location / interest in the vasculature
- 202 Positioning the sheath within a lumen / the catheter
- 203 Advancing the catheter and the self-expanding sheath in tandem over the guidewire
- 204 Distally moving the distal end / the self-expanding sheath out from the lumen / the catheter thereby causing the self-expanding sheath to move from a collapsed state within the catheter to an expanded state outside the catheter
- 205 Removing the self-expanding sheath from the catheter and the guidewire once the catheter and self-expanding sheath have been delivered to the location / interest forming a void between the guidewire and the catheter
- 206 Advancing a therapeutic mechanism through the catheter and over the guidewire

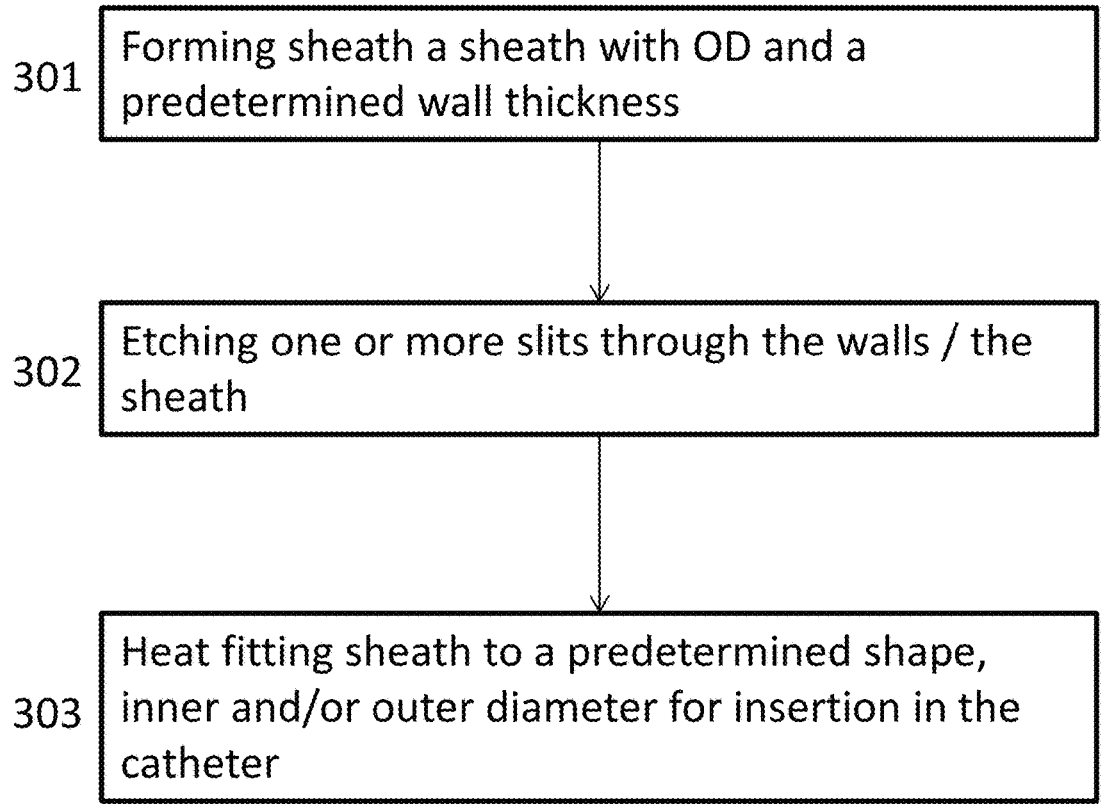

SYSTEM AND METHOD FOR DELIVERING A CATHETER

CROSS-REFERENCE TO RELATED APPLICATIONS

The present application is a Divisional of U.S. patent application Ser. No. 15/407,728 filed Jan. 17, 2017, the contents of which are incorporated herein by reference in their entirety.

FIELD

This disclosure relates to medical instruments, and more particularly, guidewire and catheter delivery systems.

BACKGROUND

Catheters can be pliable tubular structures that enter vasculature of a patient. Catheters can be used for a variety of purposes and applications. For example, they can be introduced into a particular area of interest within a vasculature and then act as a guide for introducing other peripheral, central venous, or arterial devices therein through its lumen. Such devices can include single or multi-lumen catheters, clot capturing devices, balloon catheters, and the like.

During certain procedures, a guidewire is typically introduced first separate from the catheter. Catheters and guidewires can range in size and diameter, depending on a particular procedure and area of interest in the vasculature. In a clinical setting, tracking of catheters over a guidewire can lead to complications since step movement between the larger catheter and smaller guidewire can lead to injuries to the vessel wall.

Additionally, previous approaches have permitted the guidewire to move within the catheter during delivery even upon the slightest pressure from the guidewire to the catheter. In turn, this risks injury to the patient. In typical guidewire-catheter systems, the guidewire is normally loose within the lumen of the catheter during delivery of the catheter and therefore susceptible to what is understood as step movement. However, because catheters can range in size depending on the therapeutic mechanisms they may deliver, larger outer diameters of the catheter unfortunately result in larger step movements between the guidewire that prevent safe delivery within the vasculature. This step movement can unnecessarily risk injuring the vessel wall or otherwise resulting in ineffective treatment.

Previous approaches, including those described in U.S. Pat. No. 7,731,707, have failed to resolve the issues related to step movement between the catheter and guidewire. For example, the '707 patent is directed towards creating a space in the vasculature itself as opposed to delivering a surface that extends beyond the outer diameter of the catheter for resolving step movement between a guidewire and catheter. Additionally, the '707 patent fails to teach or reasonably suggest any element that resolves step movement between catheter, guidewire, and vessel wall.

Another disclosure is also seen in U.S. Pat. Pub. 2007/0021685, wherein a catheter balloon is used with a catheter. During peripheral vasculature or coronary procedures, it can be desirous for a catheter balloon to be stationary relative to the guidewire. However, in practice, because the balloon does tend to move, the '685 publication sought to resolve this movement by implementing a break inside of the balloon and by pulling on the wire at the end. In so doing, the lumen of the catheter in the '685 publication is caused to expand into a locked state. This is strictly done to avoid longitudinal movement of the balloon within the lumen, when the balloon inflates, since the balloon is then trapped in the '685 publication by the wire inside the balloon. Unfortunately, expansion and activation is only caused in the '685 publication by manually pulling on or applying tension to the wire. Additionally, in procedures that involve catheter balloons and guidewires, the guidewire must be at the location of interest first and then the balloon is tracked over the wire.

Accordingly, in the process of tracking the guidewire, a self-expanding balloon would never actually be outside the catheter or address step movement between catheter and guidewire since doing so would run counter to the specific order of operations in procedures that mirror the '685 publication. For example, if the balloon in the '685 publication did expand outside the catheter, it would be difficult to track to the catheter or to the vasculature without risking injury to the vessel walls.

Therefore, there remains a need for new devices to safely and effectively advance catheters to locations of interest when used with guidewires to resolve these and other problems of the art.

SUMMARY

In some aspects, the present disclosure relates to a catheter delivery system. The system can include a guidewire. A catheter with a lumen is also included, the catheter having a distal end and a proximal end. A self-expanding sheath may also be slidably disposed in the lumen, the self-expanding sheath having a distal end and a proximal end. The self-expanding sheath can be capable of moving from a collapsed state within the catheter to an expanded state outside the catheter during deployment with an outer diameter greater than an inner diameter of the catheter. In certain embodiments, the outer diameter of the sheath in the expanded stated may be approximately equal to or slightly larger than the outer diameter of the catheter. The self-expanding sheath and the catheter can be advanceable in tandem over the guidewire. In this respect, as the distal end of the self-expanding sheath is moved distally relative to the catheter, the self-expanding sheath expands to the expanded state.

In the collapsed state, the outer diameter of the self-expanding sheath can be substantially snug with the inner diameter of the catheter. The distal end of the self-expanding sheath can also included a convoluted tip. The tip may be tapered with the distal end including an inner diameter substantially snug with the guidewire. In certain embodiments, the guidewire and/or the inner diameter of the sheath can include a lubricant. The outer diameter of the sheath and/or the inner diameter of the catheter can also or separately include a lubricant. The self-expanding sheath can have a radiopaque band proximal to the distal end.

The self-expanding sheath may include a plurality of slits, wherein as the self-expanding sheath is moved distally away from the distal end of the catheter, the slits can cause the outer diameter of the sheath to expand so it is greater than the inner diameter of the catheter. Also, moving to the expanded state can cause the self-expanding sheath to impart an outward force to the vessel wall. In this respect, the catheter can be released from the vessel wall. The slits can be etched longitudinally and disposed between proximal and distal ends of the self-expanding sheath. The slits can also be spiral etches or curved etches disposed between proximal and distal ends of the self-expanding sheath. The slits of each embodiment can enhance flexibility of the self-expanding sheath where otherwise adding a sheath would risk rendering the catheter too rigid for use in the tortuous vessels.

In some embodiments, the self-expanding sheath may be movable so that its distal end is capable of being distal of the distal end of the distal end of the catheter. Moving the distal end of the self-expanding sheath a predetermined distance away from the distal end of the catheter can cause the outer diameter of the self-expanding sheath to be greater than the outer diameter of the catheter.

In other embodiments, a self-expanding sheath is disclosed for use with a catheter and a guidewire. The sheath can include an outer surface slidably disposable in a lumen of the catheter. An expandable element may also be disposed on a distal end of the self-expanding sheath, the expandable element capable of moving from a collapsed state within the lumen to an expanded state outside the lumen during deployment. An outer diameter of the expandable element can be greater than an outer diameter of the catheter. The self-expanding sheath may be capable of being advanced in tandem with the catheter over the guidewire such that as the distal end of the self-expanding sheath is moved distally relative to the catheter, the self-expanding sheath can deploy or move to the expanded state. The expandable element can include a plurality of slits etched between distal and proximal ends of the sheath. As the self-expanding sheath is moved distally away from the distal end of the catheter, the slits cause the outer diameter of the sheath to be greater than the inner diameter of the catheter. In the expanded state, the slits can cause the sheath to form a "pear-like" shape.

In other embodiments, a method is disclosed for delivering a catheter to a location of interest in the vasculature. The method can include selectively positioning a guidewire at the location, positioning a self-expanding sheath within a lumen of the catheter, advancing the catheter and the self-expanding sheath in tandem over the guidewire, and distally moving a distal end of the self-expanding sheath out from the lumen of the catheter thereby causing the self-expanding sheath to move from a collapsed state within the catheter to an expanded state outside the catheter.

The method can also include having an outer surface of the self-expanding sheath contact the distal end of the lumen as the sheath is deployed so that the sheath separates the catheter from the vessel walls. In certain embodiments, the method can also include forming a plurality of slits on the self-expanding sheath between its proximal and distal ends, and the slits causing the self-expanding sheath to expand to the expanded stated with an outer diameter greater than the outer diameter of the catheter. The method may also include extending the distal end of the sheath beyond a distal end of the catheter thereby smoothening a transition between the catheter and the guidewire during delivery. The method can also include removing the self-expanding sheath from the catheter and the guidewire once the catheter and self-expanding sheath have been delivered to the location of interest forming a void between the guidewire and the catheter. Finally, the method can include the self-expanding sheath imparting an outward expansion force to the vessel wall as the self-expanding sheath moves to the expanded state.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 1 is a partial perspective view of an example embodiment of the catheter system disclosed herein, wherein the sheath is being deployed from the catheter.

FIG. 2 is a partial side plan view of the system shown in FIG. 1.

FIG. 15 is a flow diagram for a method of delivering a catheter to a location of interest in the vasculature.

FIG. 16 is a flow diagram for a method of manufacturing a self-expanding sheath.

DETAILED DESCRIPTION

Figure 3:
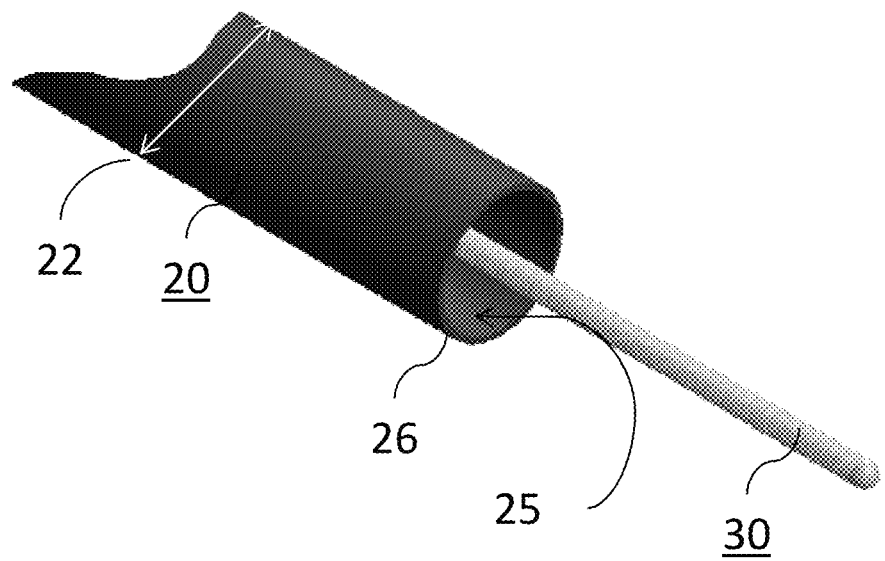
FIG. 3 is a partial perspective view of the catheter and guidewire of FIGS. 1-2 without the sheath.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braided stent body to the vasculature of a subject.

The method and systems disclosed herein are directed towards minimizing or eliminating the step between a catheter and corresponding guidewire and to form a backward step. A guidewire can be selectively positioned at a location of interest in the vasculature. A self-expanding sheath may be assembled with a catheter by being slidably inserted therein, wherein the catheter and self-expanding sheath can then be advanced in tandem over a guidewire. The self-expanding sheath may not completely hug or contact the guidewire. While the sheath can be collapsed within the catheter, the sheath may be self-expanding so that an outer surface of the sheath can be larger than the outer surface of the catheter during deployment. In this respect, once the sheath and catheter have been positioned at the location of interest in the vasculature, the sheath can be moved distal so that it extends beyond the outer diameter (OD) of the catheter. As the sheath is deployed, it expands so that the sheath operates to separate the catheter from the vessel walls during use.

The herein disclosed system and method that incorporates the self-expanding sheath, catheter, and guidewire may be delivered to the location of interest without any corresponding therapeutic mechanisms (e.g. a balloon, coil, adhesive, or the like). Instead, the system and method disclosed herein is a safe, efficient, and cost-effective solution for delivering a catheter in tandem with a sheath disposed therein, wherein the sheath can be moved distally out from the inner lumen of the catheter so that the guidewire can safely deliver therapeutic mechanisms to the location of interest. In particular regard to procedures in the neurovasculature, vessels are typically tortuous through which catheters can be difficult to advance. By using the self-expanding sheath of this disclosure, the catheter can be safely traversed within the vasculature, tortuous or not, since the step movement is minimized between the catheter and guidewire.

Turning to FIGS. 1-2, one embodiment of the self-expanding sheath 10 is depicted assembled with the catheter 20 and guidewire 30 extended therethrough. The sheath 10 includes a proximal end 18 near the operator, and a distal end 19 disposed away from the operator. At a distal end 26 of the catheter 20 where the guidewire 30 can be caused to be deployed, the sheath 10 may be in contact at its outer surface with the inner surface of the catheter 20 at its distal end 26 as the sheath 10 expands during deployment. This is particularly advantageous in the art as catheter flexibility is necessary for tracking and maintaining patient safety during use. While adding a sheath to a guidewire-catheter system would normally surrender flexibility of the catheter when the sheath is stowed therein, the self-expanding, flexible sheath 10 described herein permits the sheath and catheter to be collectively flexible and trackable during use over the guidewire 30 within the vasculature.

The sheath 10 and the catheter 20 may be advanced in tandem over the guidewire 30 simultaneously to the location of interest (as opposed to tracking a self-expanding balloon first and then the catheter). After catheter 20 and self-expanding sheath 10 are advanced to the location of interest, the sheath 10 can then be advanced distally away from the catheter 20 a predetermine distance so that it self-expands a predetermined amount OD at the distal end of the catheter 20 that is greater than the OD of the catheter. In turn, any step movement between the guidewire 30 and catheter 20 is all but eliminated when the catheter 20 is being advanced thereover to the location of interest. The sheath 10 described herein can be used over the guidewire 30 so as to minimize the step between OD of the guidewire 30 and ID of the catheter 20 to facilitate safe insertion of a venous device into vasculature of a patient.

The snug fit between sheath 10, catheter 20, and guidewire 30 ensures that the guidewire 30 does not otherwise injure the patient. Specifically, system and methods of this disclosure are directed towards different procedures altogether without catheter balloons. In the system and methods of this disclosure, catheter 20 may be any biocompatible material known, including a polymeric material such as polyethylene, polypropylene, polystyrene, polyester, polyurethane, polyamide, peboxes, and the like. For example, the catheter 20 can be formed from a rubber or a plastic such as fluorinated ethylene-propethylene (FEP), polyethylene (PE), or the like. Catheter 20 can be elongate and/or tubular with an inner lumen 25 that extends longitudinally through catheter 20. Catheter 20 can have an OD 22 and an ID 24 defined by lumen 25.

The self-expanding sheath 10 may have an inner lumen 12, wherein the sheath 10 can have an OD 6 and an ID 8. Sheath 10 may be may be any biocompatible material known, including a polymeric material such as polyethylene, polypropylene, polystyrene, polyester, polyurethane, polyamide, peboxes, and the like. Sheath 10 may be capable of extending internally along catheter 20. A distal end 19 of sheath 10 may extend beyond a distal end 24 of catheter 20 thereby avoiding a blunt transition between catheter 20 and guidewire 30. It is understood that sheath 10 may be movable within catheter 20, fixed in place, or movable between a plurality of predetermined positions.

The OD 6 of sheath 10 can be disposed inside catheter 20 before or while catheter is disposed in the vasculature of the patient. The OD 6 of the sheath 10 may be configured to fit snugly within the catheter 20 so as to minimize the step or distance between the sheath 10 and catheter 20. In some embodiments, the OD 6 of sheath 10 may be substantially similar to the ID 22 of catheter 20. Sheath 10 may also be partially or substantially covered with a lubricant coating or be constructed from a material that induces movement between sheath 10 and catheter 20.

Sheath 10 may also include a radio opaque portion 40. Portion 40 may be one or more bands or selected areas of sheath 10 constructed from a radio opaque material. Portion 40 can be disposed about sheath 10 to facilitate the fluoroscopic observation thereof during a procedure. Another radiopaque marker can be provided on catheter 20 to fluoroscopically determine the location of guidewire 30 and/or catheter 20. Guidewire 30 may be any guidewire as is known in the art, including being elongated, constructed of any relatively rigid material including metals. Guidewire 30 may be any shape and may have a constant stiffness or flex.

Sheath 10 may be formed from one material or from a blend of materials selectively positioned for operable for positioning within catheter 20 when disposed in the vasculature of a patient. In certain embodiments, sheath 10 can be formed from a material that becomes softer with warmer temperatures but is substantially rigid outside the patient. Typical materials can include polyurethane, polytetrafluor-ethylene (PTFE), FEP, or PE.

Figure 4:
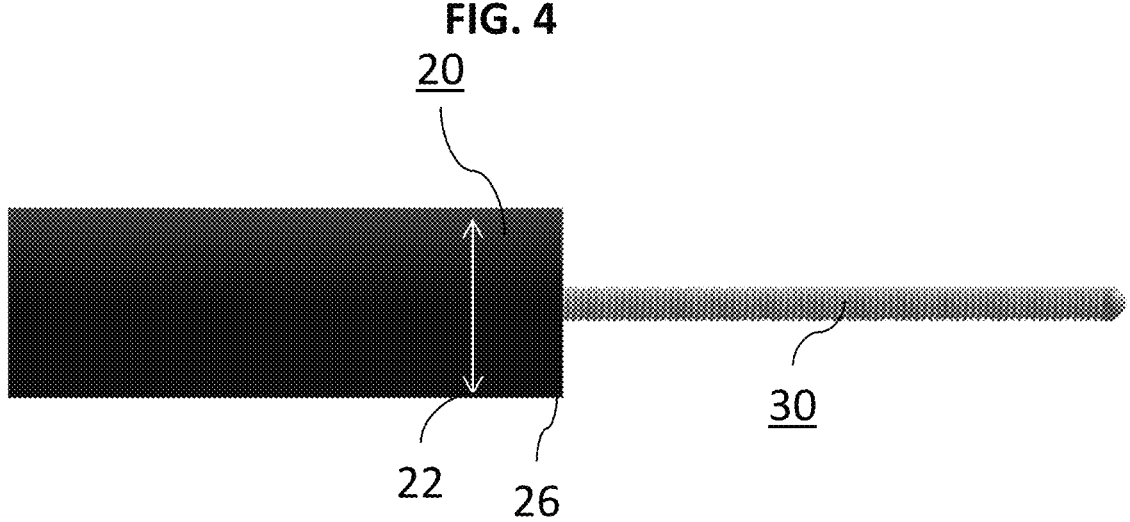
FIG. 4 is a partial side plan view of the catheter and guidewire of FIGS. 1-2 without the sheath.

Once the catheter 20 and self-expanding sheath 10 have been delivered to the location of interest, the self-expanding sheath 10 may be removed from the catheter and the patient thereby leaving a space between the guidewire and catheter to carry out the required procedure and deliver therapeutic mechanisms thereto. This can be more clearly seen in FIGS. 3 and 4, wherein a partial perspective view of system 1 is shown whereby sheath 10 has been removed leaving only guidewire 30 and catheter 20. This space that is defined between the guidewire 30 and ID 24 of catheter 20 can accommodate various therapeutic mechanisms that may be desired for delivery to the location of interest for the relevant procedure. Thus, in one example, the self-expanding sheath 10 cannot and does not provide or deliver any therapeutic mechanisms to the patient. It can be solely used to deliver the catheter 20 along the guidewire 30 to the location of interest.

Figure 5:
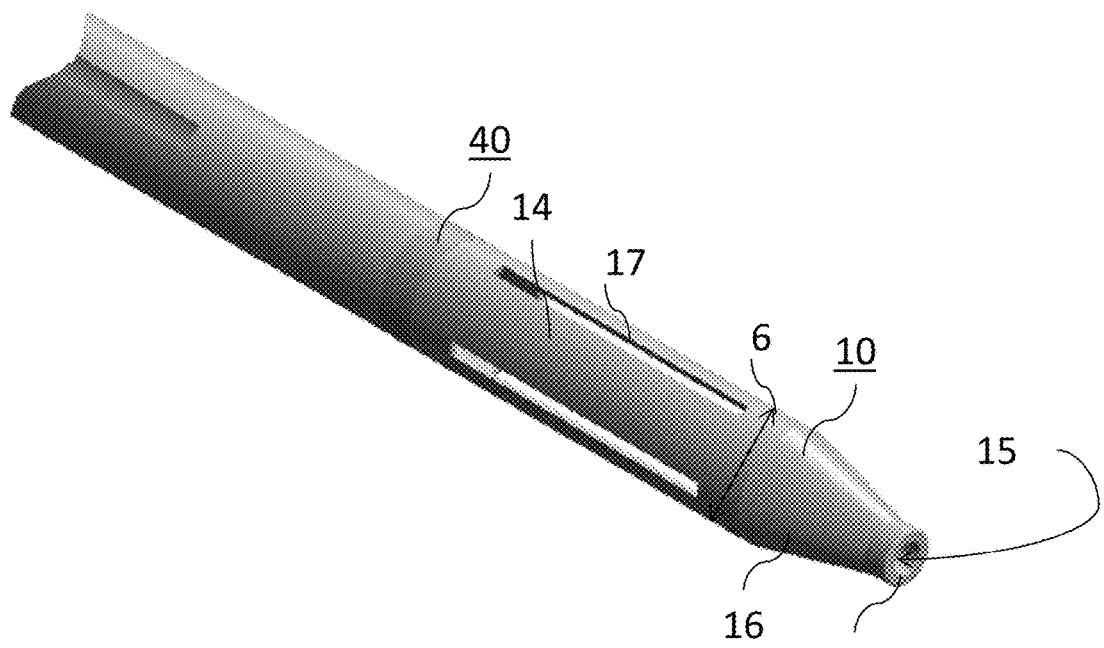
FIG. 5 is a partial perspective view of a sheath in a collapsed state.
Figure 6:
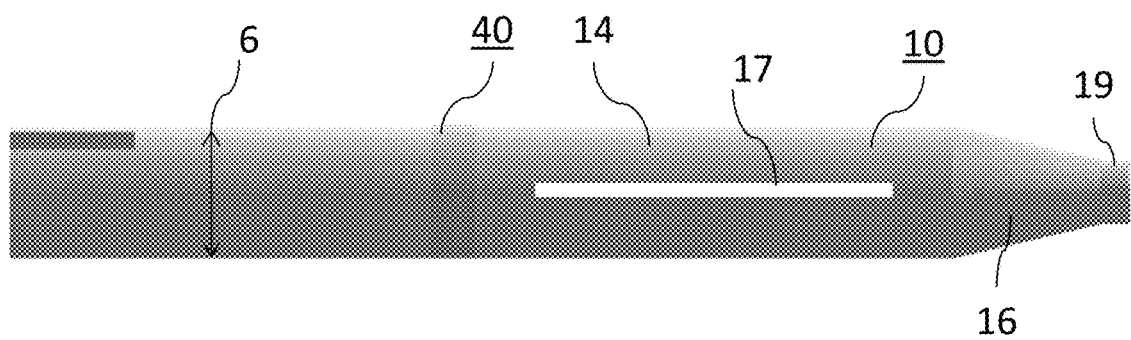
FIG. 6 is a side plan perspective view of a sheath in a collapsed state.

A convoluted tip 16 can be located at the distal end 19 of sheath 10. In FIGS. 1-2, tip 16 can be seen as tapering from OD 6 to a smaller diameter at its distal end 19 about guidewire 30. This is more clearly seen in FIGS. 5-6 which show sheath 10 alone, unassembled with catheter 20 and guidewire 30. Specifically, FIG. 5 depicts a partial perspective view of sheath 10 and FIG. 6 depicts a partial side plan view of sheath 10. Tip 16 is disposed adjacent sidewalls 14 which may be substantially non-convoluted or tubular along the ID 22 of catheter 20. Sidewalls 14 can be circular or tubular but sheath 10 is not so limited and may be any shape, including oblong shapes, depending on the corresponding catheter 20. Sidewalls 14 include one or more slits 17 or cutouts. The one or more slits 17 can extend partially or completely through sidewalls 14 and may weaken the structural integrity of sheath 10. In this regard, flexibility of sheath 10 is enhanced. Slits 17 can extend partially and/or completely axially along the OD 6 and ID 8 of sheath 10. Tip 16 can include an opening 15 operable to slide over guidewire 30. Step movement is substantially limited, if not eliminated, as between opening 15 of the distal end 19 of sheath 10 and guidewire 30 since the ID of opening 15 of sheath 10 is slightly larger than the OD of the guidewire 30. In certain embodiments, a gap of about 0.0002"-0.001" can exist between guidewire 30 and the ID of the opening of the sheath 10 thereby permitting the guidewire 30 to move independently of the sheath 10.

Slits 17 may be self-expanding and etched longitudinally between distal and proximal ends of the sheath 10. The slits 17 may be integrally formed with the sheath 10. The sheath 10 may also be constructed from a single, unitary material. In certain embodiments, the sheath 10 with its one or more slits 17 may impart a predetermined outward force to the vessel wall as it expands when being slid distally out of the catheter 20 during use. In certain embodiments, the slits 17 may be formed with the sheath 10 so that the sheath 10 in a deployed, expanded state takes a "pear-like" shape. However, sheath 10 is not so limited and the sheath 10 may take any shape as needed or required in an expanded state that can expand the vasculature to move catheter 20 from contacting the vessel walls. Longitudinal slits 17 are particularly advantageous from a manufacturing and design perspective since they minimize complexity without sacrificing the self-expanding nature of the sheath when used in a system with a catheter and guidewire.

Figure 7:
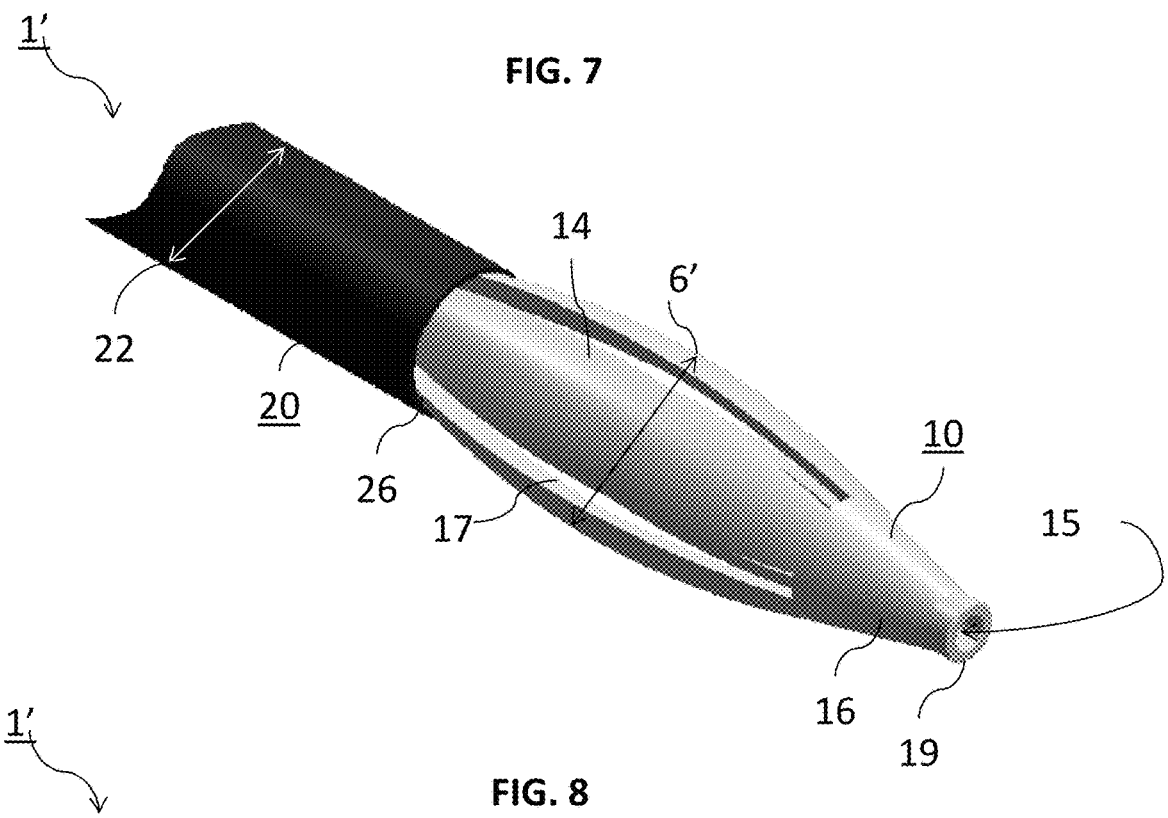
FIG. 7 is a partial perspective view the catheter system disclosed herein, wherein the sheath is deployed from the catheter in an expanded state.
Figure 8:
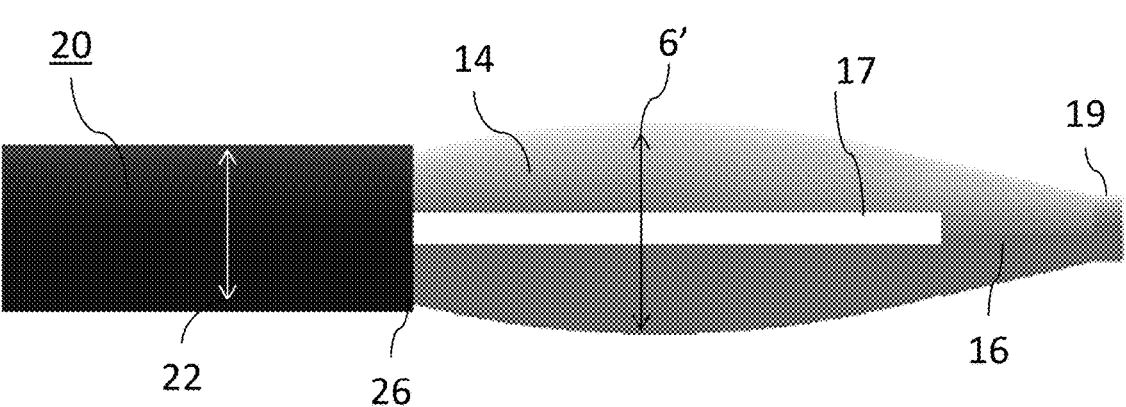
FIG. 8 is a partial side plan view of the system shown in FIG. 7.

In FIGS. 7-8, system 1 is depicted with sheath 10 having been moved distally away from catheter into the expanded state. FIG. 7 in particular depicts a perspective view of sheath 10 in an expanded state and assembled with guidewire 30 and catheter 20. FIG. 8 depicts a side plan view of the system 1 shown in FIG. 7. Sheath 10 may be operable to move between a compressed state within the catheter 20 and a deployed state outside of the catheter 20. OD 6' of the sheath 10 in the deployed state may be a predetermined ratio greater than the OD 22 of the catheter 20. However, in the deployed state, the sheath 10 does not exhibit outward pressure such as, for example, a catheter balloon that imparts pressures to vessel walls of the vasculature.

Figure 9:
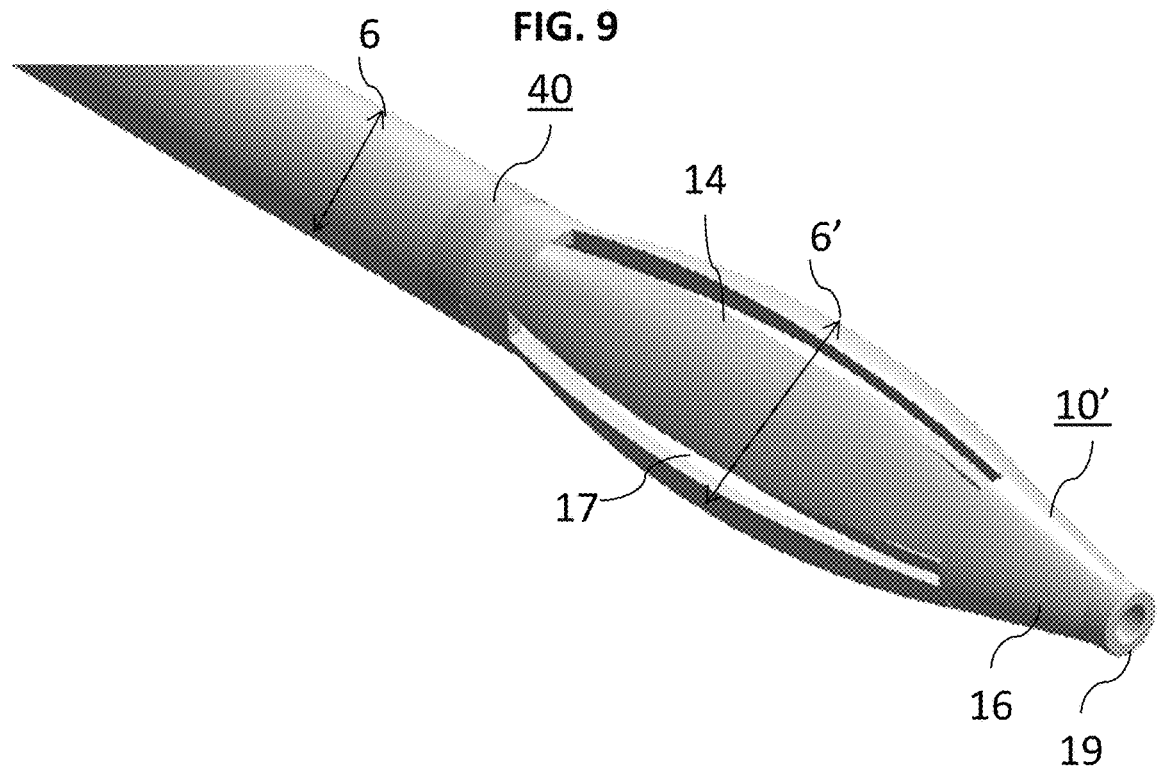
FIG. 9 is a partial perspective view of a sheath in an expanded state.
Figure 10:
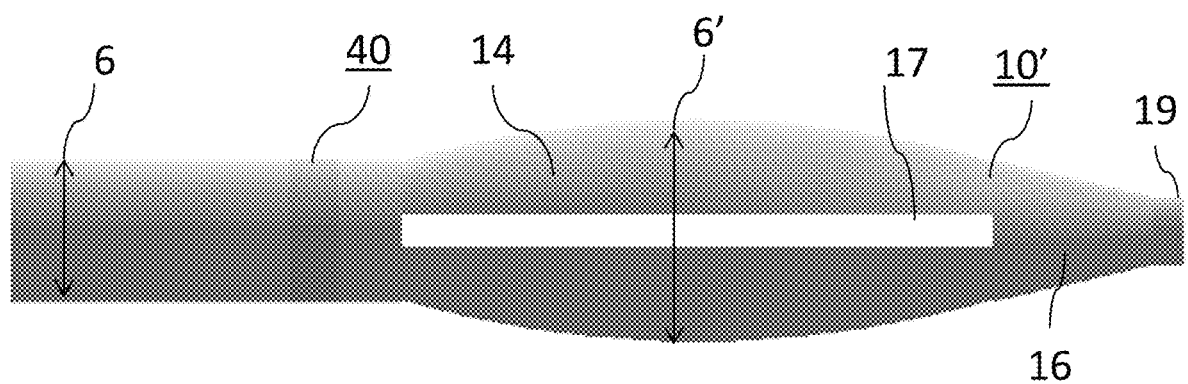
FIG. 10 is a side plan perspective view of the sheath in FIG. 9.

Turning to FIGS. 9-10, sheath 10' is depicted alone in an expanded state unassembled with catheter 20 and guidewire 30. Specifically, FIG. 9 depicts a partial perspective view of sheath 10' and FIG. 10 depicts a partial side plan view of sheath 10'. Sidewalls 14 expand as slits 17 are moved distally away from catheter 20 thereby causing its OD 6 to expand to expanded OD 6'. In the expanded state, as shown, sheath 10' may take a "pear-like", elliptical shape with its central portion having an OD substantially greater than the OD associated with distal end 19 and/or portion 40. However, sheath 10' is not so limited and sheath 10' may take any shape or assume any OD that is at least greater than OD 22 of catheter 20 so that sheath 10' is capable of imparting an outward force to the vessel walls during deployment from catheter 20.

Figure 11:
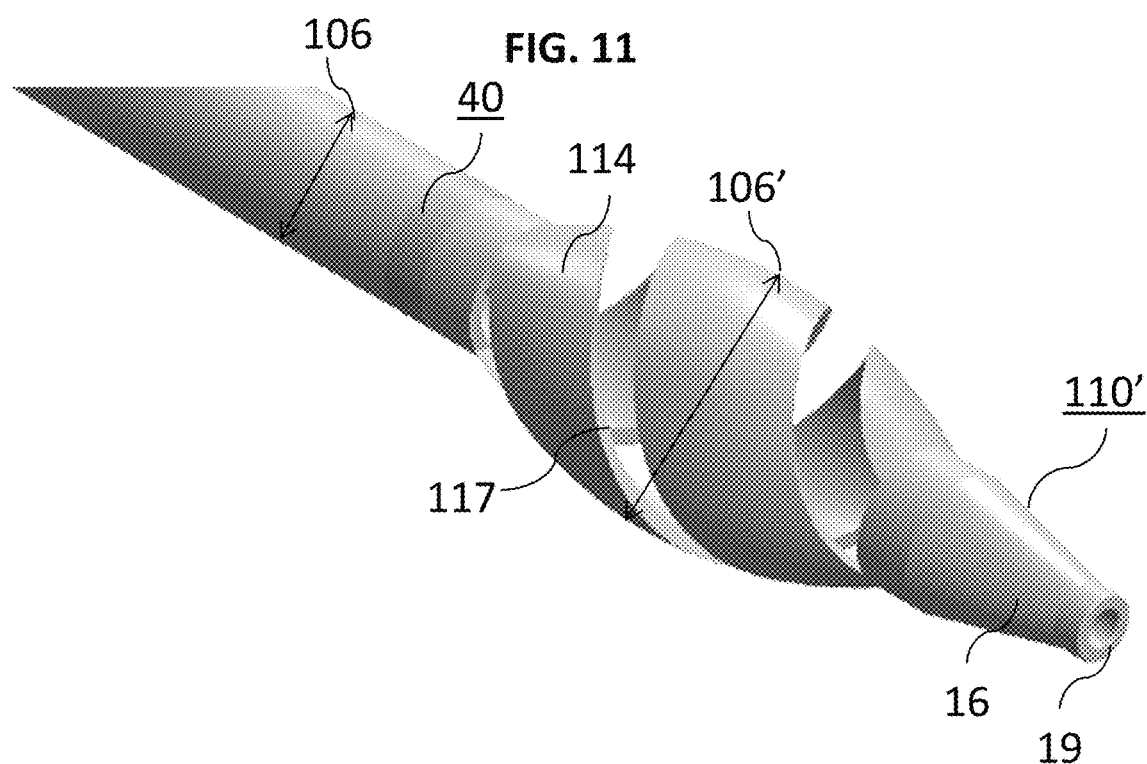
FIG. 11 is a partial perspective view of another exemplary sheath in an expanded state.
Figure 12:
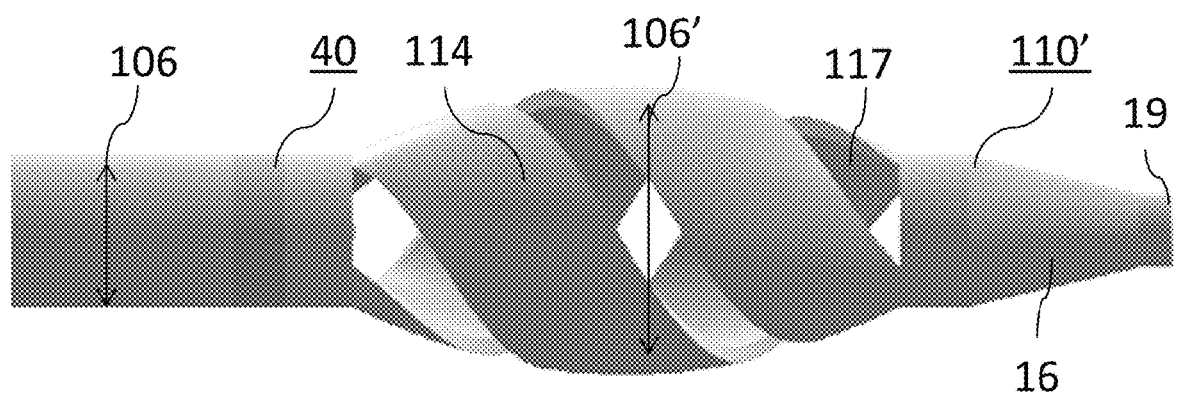
FIG. 12 is a side plan perspective view of the sheath in FIG. 11.

Turning to FIGS. 11-12, another sheath 110' is depicted alone in an expanded state unassembled with catheter 20 and guidewire 30. Specifically, FIG. 11 depicts a partial perspective view of sheath 110' and FIG. 12 depicts a partial side plan view of sheath 110'. Instead of being longitudinally etched, slits 117 may be spiral or curved slits etched into sidewalls 114 of sheath 110'. As a result, sidewalls 114 expand as slits 117 are moved distally away from catheter 20 thereby causing its OD 6 to expand to expanded OD 6'. In the expanded state, as shown, sheath 110' may take a "pear-like", elliptical shape with its central portion having an OD substantially greater than the OD associated with distal end 119 and/or portion 40. However, sheath 110 is not so limited and sheath 110' may take any shape or assume any OD that is at least greater than OD 22 of catheter 20 so that sheath 110' is capable of imparting an outward force to the vessel walls during deployment from catheter 20.

Figure 13:
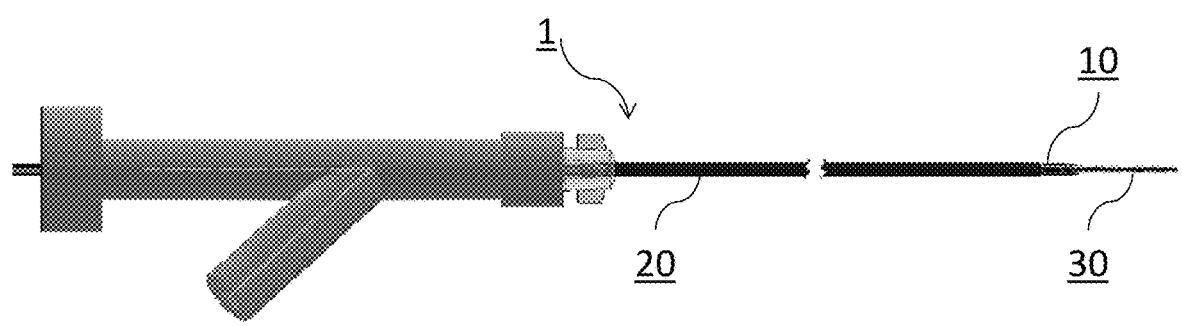
FIG. 13 is a side plan view of an example embodiment of the catheter system disclosed herein in combination with an exemplary delivery system, wherein the sheath and catheter are compressed.
Figure 14:
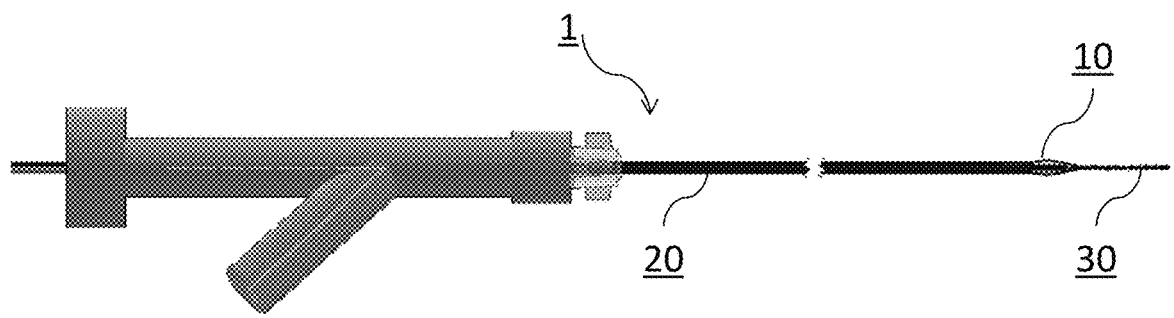
FIG. 14 is a side plan view of an example embodiment of the catheter system disclosed herein in combination with an exemplary delivery system, wherein the sheath and catheter are in an expanded state.

Turning to FIGS. 13 and 14 are side plan views of an example catheter system 1 in combination with an exemplary delivery system, wherein the sheath 10 and catheter 20 in FIG. 13 are compressed but in the process of being deployed. FIG. 14 shows the sheath 10 and catheter 20 in an expanded state following deployment from the delivery system.

Turning to FIG. 15 is a method 200 of delivering catheter 20 to a location of interest in the vasculature. The method can include (201) selectively positioning guidewire 30 at the location, (202) positioning sheath 10 within a lumen of the catheter 20, (203) advancing the catheter 20 and the self-expanding sheath 10 in tandem over the guidewire 30, and (204) distally moving distal end 19 of the self-expanding sheath 10 out from the lumen of the catheter 20 thereby causing the self-expanding sheath 10 to move from a collapsed state within the catheter 20 to an expanded state outside the catheter 20. The method can also include (205) removing the self-expanding sheath 10 from the catheter 20 and the guidewire 30 once the catheter 20 and self-expanding sheath 10 have been delivered to the location of interest forming a void between the guidewire 30 and the catheter 20. The method can also include (206) advancing a therapeutic mechanism through the catheter 20 and over the guidewire 30.

Turning to FIG. 16, a method 300 is disclosed for manufacturing sheath 10, 110 for use in a system 1 with guidewire 30 and catheter 20. The method may include step 301 wherein sheath 10, 110 is formed with OD 6, 106 and a predetermined wall thickness. Then, in step 302 one or more slits 17, 117 can be etched through the walls of the sheath 10, 110. In step 303, sheath 10, 110 may be heat fit to a predetermined shape, inner and/or outer diameter for insertion in the catheter 20. Sheath 10, 110 may have a predetermined resiliency and/or flexibility. During use, sheath 10, 110 and catheter 20 may be advanced in tandem over guidewire 30 to a location of interest in the vasculature, wherein sheath 10, 110 can be moved distally passed distal end 26 of catheter 20 thereby causing sheath 10, 110 to move from a first OD 6, 106 and second, greater OD 6', 106' that is larger than OD 22 of catheter 20.

The systems and methods of this disclosure also contemplate a catheter system 500 that may be a kit that includes catheter 20 and one or more of sheaths 10, 110. Each sheath 10, 110 can be separately, selectively inserted within catheter 20. Each sheath 10, 110 can range in terms of diameter and/or any of the previously disclosed shapes. A kit may include a plurality of sheathes (e.g. 10 sheathes) that are separately sized so that a given sheath can be selected and positioned as required for different sized guidewires.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method of delivering a catheter to a location of interest in a patient's vasculature, the method comprising:
    positioning a self-expanding sheath within a lumen of the catheter;
    advancing the catheter and the self-expanding sheath in tandem over a guidewire;
    distally moving a distal end of the self-expanding sheath out from the lumen of the catheter thereby causing the self-expanding sheath to move from a collapsed state within the catheter to an expanded state outside the catheter; and
    removing the self-expanding sheath from the catheter and the guidewire once the catheter and self-expanding sheath have been delivered to the location of interest forming a void between the guidewire and the catheter,
    wherein when the self-expanding sheath is in the expanded state both the self-expanding sheath and the catheter are distally advanceable in tandem.

2. The method of claim 1, further comprising: contacting an outer surface of the self-expanding sheath to the distal end of the lumen of the catheter as the sheath is deployed, and separating the catheter from the vessel walls with the deployed sheath.

3. The method of claim 1, further comprising: forming a plurality of slits on the self-expanding sheath between a proximal end and a distal end; and
    causing, by the slits, the self-expanding sheath to expand to the expanded state with an outer diameter greater than the outer diameter of the catheter.

4. The method of claim 3, further comprising:
    causing, by the slits, the self-expanding sheath to form a "pear-like" shape in the expanded state.

5. The method of claim 1, further comprising: extending the distal end of the sheath beyond a distal end of the catheter thereby smoothing a transition between the catheter and the guidewire during delivery.

6. The method of claim 1, further comprising: the self-expanding sheath imparting an outward expansion force to a vessel wall as the self-expanding sheath moves to the expanded state.

7. The method of claim 1, the self-expanding sheath being a polymeric self-expanding sheath.

8. The method of claim 1, wherein a distal end of the self-expanding sheath comprises a tapered tip comprising a diameter smaller than a diameter of a distal portion of the sheath, the distal end comprising an inner diameter that is approximately the same diameter as a diameter of the guidewire.

9. The method of claim 8, further comprising: including a lubricant in at least one of the guidewire, an inner diameter of the sheath, the outer diameter of the sheath, and the inner diameter of the catheter.

10. The method of claim 1, wherein the self-expanding sheath comprises a radiopaque band proximal to a distal end of the sheath.

11. The method of claim 1, the self-expanding sheath comprising:
    a self-expanding sidewall in a distal portion of the sheath capable of moving from a collapsed state within the catheter to an expanded state outside the catheter during deployment with an outer diameter greater than an outer diameter of the catheter,
    the self-expanding sidewall further comprising a plurality of longitudinally etched slits in the self-expanding sidewall thereby weakening structural integrity of the self-expanding sidewall while enhancing flexibility,
    the slits defining segments of the self-expanding sidewall each having a respective arcuate cross section in a plane orthogonal to a longitudinal axis of the sheath.

12. The method of claim 11, further comprising:
    causing, by the slits, the expandable element to form a "pear-like" shape in the expanded state.

13. The method of claim 1, the self-expanding sheath comprising:
    an expandable element disposed on a distal portion proximate to a distal end of the self-expanding sheath, the expandable element capable of moving from a collapsed state within the lumen to an expanded state outside the lumen during deployment,
    the expandable element comprising a self-expanding sidewall comprising slits therein to define segments of the self-expanding sidewall each having a respective arcuate cross section in a plane orthogonal to a longitudinal axis of the sheath.

14. The method of claim 13, further comprising:
causing, by the slits, the outer diameter of the expandable element to be greater than the inner diameter of the catheter as the self-expanding sheath is moved distally away from the distal end of the catheter.

15. A method of delivering a catheter to a location of interest in a patient's vasculature, the method comprising:
positioning a self-expanding sheath within a lumen of the catheter;
advancing the catheter and the self-expanding sheath in tandem over a guidewire; and
distally moving a distal end of the self-expanding sheath out from the lumen of the catheter thereby causing the self-expanding sheath to move from a collapsed state within the catheter to an expanded state outside the catheter,
wherein when the self-expanding sheath is in the expanded state both the self-expanding sheath and the catheter are distally advanceable in tandem, and
wherein the self-expanding sheath comprises:
a distal portion proximate a distal end of the sheath; and
a self-expanding sidewall in the distal portion comprising slits therein to define segments of the self-expanding sidewall each having a respective arcuate cross section in a plane orthogonal to a longitudinal axis of the sheath.

16. The method of claim 15, further comprising:
moving the self-expanding sidewall from a collapsed state within the catheter to an expanded state outside the catheter during deployment with an outer diameter greater than an outer diameter of the catheter.

17. The method of claim 16, further comprising:
causing, by the slits, the expandable element to form a "pear-like" shape in the expanded state.

18. The method of claim 15, further comprising: removing the self-expanding sheath from the catheter via a proximal end of the catheter.

19. A method of delivering a catheter to a location of interest in a patient's vasculature, the method comprising:
distally moving a distal end of a self-expanding sheath out from the catheter thereby causing the self-expanding sheath to move from a collapsed state within the catheter to an expanded state outside the catheter;
distally advancing the self-expanding sheath and the catheter in tandem when the self-expanding sheath is in the expanded state; and
removing the self-expanding sheath from the catheter and the guidewire once the catheter and self-expanding sheath have been delivered to the location of interest forming a void between the guidewire and the catheter,
wherein when the self-expanding sheath is in the expanded state both the self-expanding sheath and the catheter are distally advanceable in tandem.

\* \* \* \* \*